United States Patent [19]

Christell et al.

[11] 4,028,267
[45] June 7, 1977

[54] METHOD AND APPARATUS FOR MEASURING THE CONCENTRATION OF A COMPONENT, FOR INSTANCE IRON, IN A MATERIAL

[75] Inventors: Adolf Ragnar Roland Umberto Einarsson Christell, Stockholm; Kaijo Aatto Matias Koski, Tyreso; Knut Lennart Ljunggren, Stockholm, all of Sweden

[73] Assignee: Stiftelsen Isotoptekniska Laboratoriet, Stockholm, Sweden

[22] Filed: Mar. 27, 1975

[21] Appl. No.: 562,460

[30] Foreign Application Priority Data

Apr. 9, 1974 Sweden .............................. 7404824

[52] U.S. Cl. ............................... 250/359; 250/308
[51] Int. Cl.² ........................................ G01N 23/02
[58] Field of Search ........... 250/308, 359, 360, 390, 250/391, 392

[56] References Cited

UNITED STATES PATENTS

| | | |
|---|---|---|
| 3,009,062 | 11/1961 | Brooksbank, Jr. et al. ........ 250/392 |
| 3,256,434 | 6/1966 | Carver et al. ...................... 250/390 |
| 3,668,401 | 6/1972 | Shah et al. ...................... 250/308 X |
| 3,794,843 | 2/1974 | Chen ............................. 250/392 X |

Primary Examiner—Archie R. Borchelt
Attorney, Agent, or Firm—Eric Y. Munson

[57] ABSTRACT

Method and apparatus for measuring the concentration of various components, such as the iron component in iron ore, by exposing the material to irradiation between a neutron source and a gamma ray detector. The emitted gamma rays are captured by the detector and transformed into a signal which is transmitted to a recording device for measuring the gamma ray radiation.

16 Claims, 5 Drawing Figures

METHOD AND APPARATUS FOR MEASURING THE CONCENTRATION OF A COMPONENT, FOR INSTANCE IRON, IN A MATERIAL

BACKGROUND OF THE INVENTION

In industrial processes it is to-day often desirable at various stages of the material handling to be able to obtain quick information regarding the concentration of various components forming part of the material, which is carried through the process in limited quantities, for instance in cars or in ships, or which moves on conveyors, in transportation ducts or the like.

Investigations have disclosed that it is possible to expose a material to neutron irradiation in order to obtain a prompt emission of gamma rays from components in the material, said gamma radiation being characteristic of the irradiated component and being also related in a certain way to the concentration of said component in the material. It is then possible firstly to produce a reference diagram by carrying out a number of measurements of the gamma radiation which is typical for the component in question at various concentrations of said component. The said reference diagram may then be utilized as a calibrating diagram for the practical measurements in question. Such a diagram for measuring the concentration of iron in a certain ore may as an example have the form illustrated in the sketch A below.

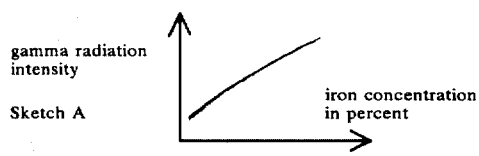

Prior experiments using a $^{239}$Pu-Be radiation source and a scintillation detector have not given sufficiently accurate results and have proved to be much too dependent on the composition of the material and on its shape. Furthermore, in the known apparatuses too little consideration has been given to the practical conditions and the safety precautions against radiation hazards.

SUMMARY

The method and apparatus defined in the claims have solved these and other problems.

We have found that by carrying out the measurement according to a certain method and by forming the apparatus for making the measurement in a certain way we can obtain a practically linear relationship between, for instance, the iron concentration and the measured gamma radiation intensity at least within certain concentration values of great practical interest.

The invention is described below with reference to the accompanying drawings which illustrate by way of example an apparatus for measuring the concentration of iron in a material forwarded on a conveyor belt. The method and apparatus according to the invention may, however, also be used for measuring the concentration of other components in a material within the scope of the claims.

DESCRIPTION OF THE PREFERRED EMBODIMENT

Figure 1:
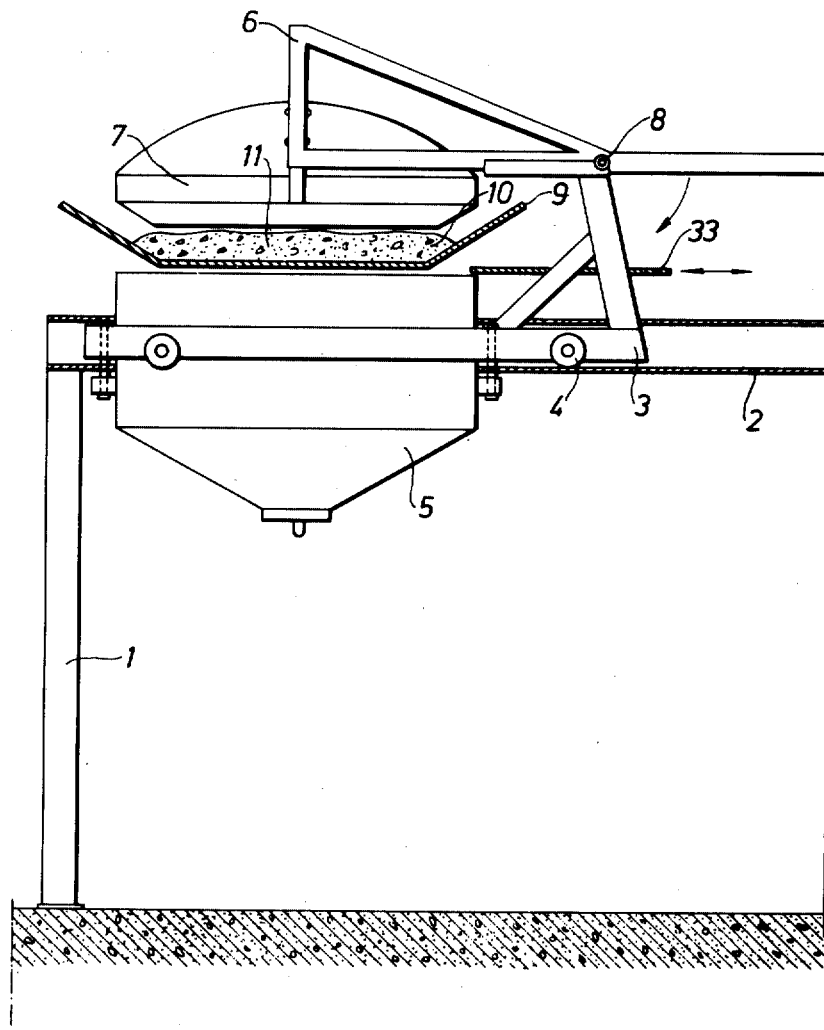
FIG. 1 is a cross section of an ore transportation conveyor and an end view of the measuring apparatus according to the invention looking in the longitudinal direction of the conveyor.
Figure 2:
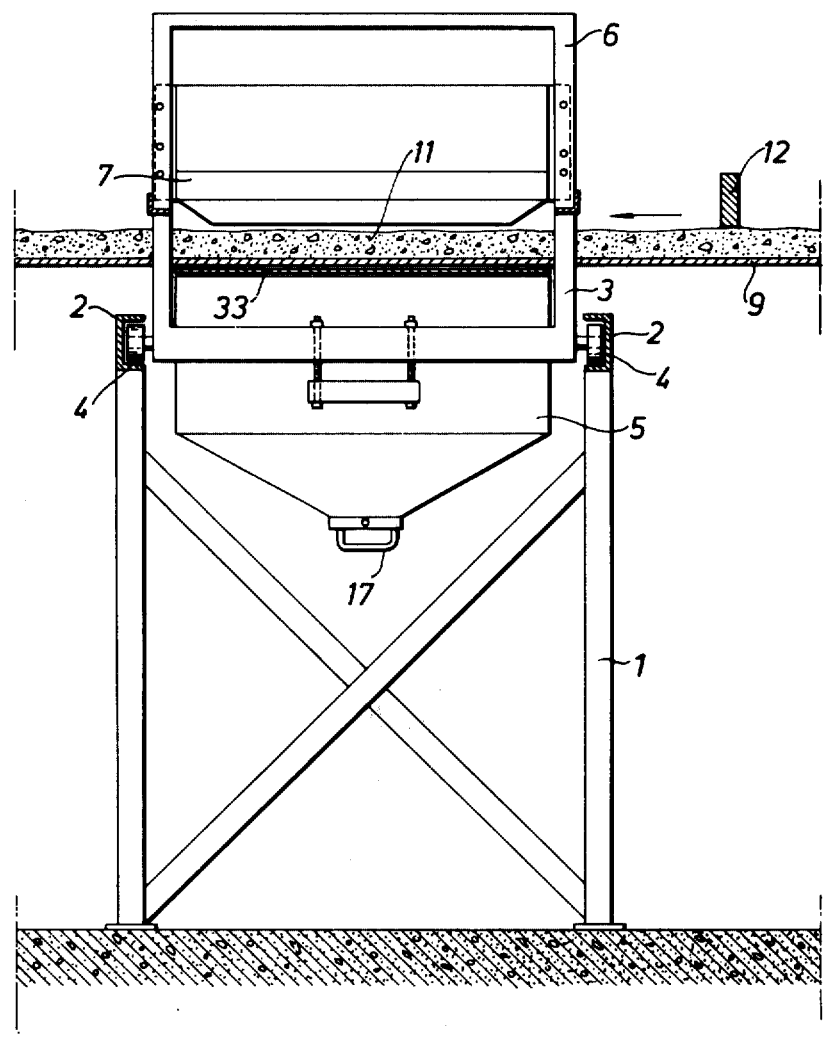
FIG. 2 is a side view of the measuring apparatus.

The measuring apparatus illustrated in the drawings consists of a frame 1, which carries two channels 2 forming rails for a carriage 3 having wheels 4 rolling on the lower flanges of the channels. The carriage 3 carries a lower aluminium sheet container 5 and an upper frame work 6 which carries an upper aluminium sheet container 7. The upper frame work 6 may be swung high on pivots 8 on the carriage, so that it may be moved together with the carriage 3 from the side over a conveyor belt 9 into a desired position in relation to the conveyor belt with the lower container immediately below the belt and the upper container immediately above the material 10 on the belt. The above mentioned mechanical arrangement of the measuring apparatus may naturally be varied in many different ways according to local conditions. In order to obtain a constant thickness of the material on the belt at the measuring location 11 between the containers 5 and 7 a scraper 12 may preferably be provided above the belt just before the measuring location 11.

Figure 3:
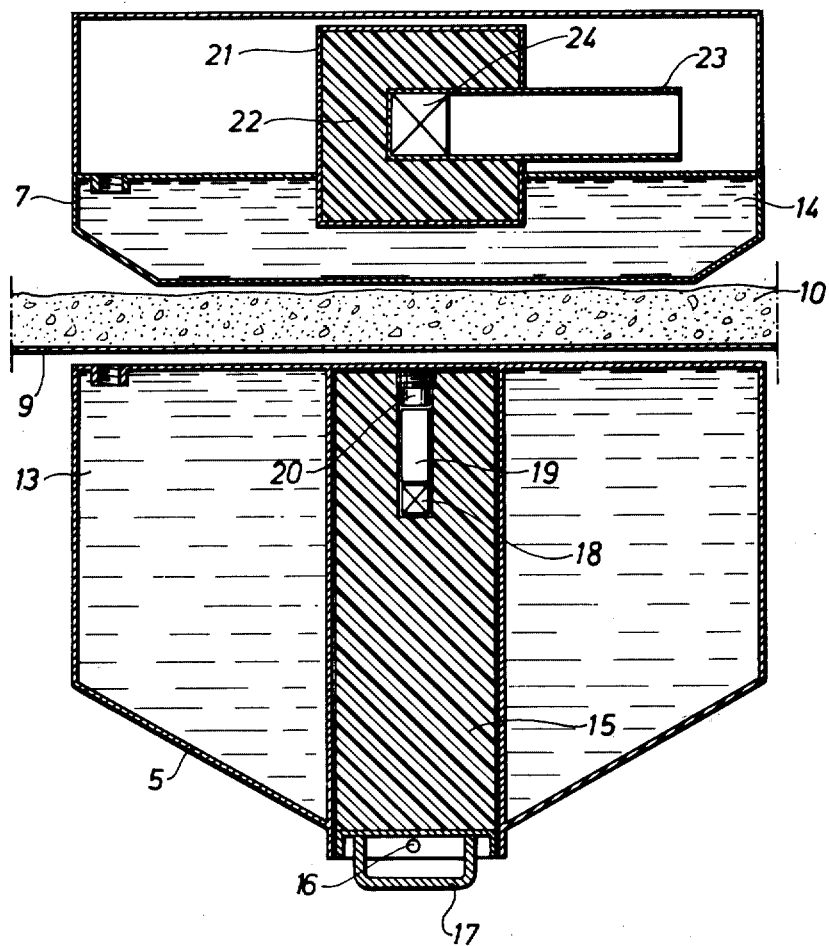
FIG. 3 is a section of the measuring apparatus in the longitudinal direction of the conveyor and FIG. 4 is a cross section of the measuring apparatus.
Figure 4:
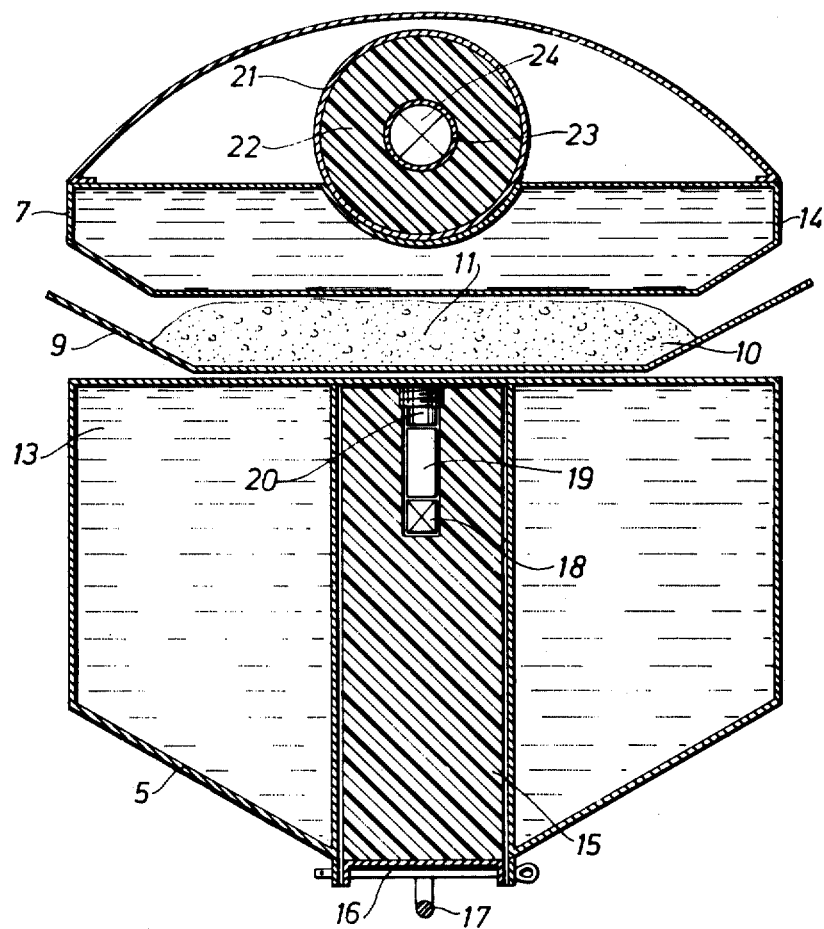

The containers 5 and 7 illustrated in longitudinal and cross section in FIGS. 3 and 4 consist of aluminium sheet containers filled with water as indicated at 13 and 14. The container 5 has a vertical through opening in which a unit or plug 15 of polythene or paraffin or other suitable material which is rich in hydrogen is fitted and fixed by means such as a sealed bolt as indicated at 16. The plug 15 is provided with a handle 17 in order to make possible an easy and quick removal of the plug, for instance in case of an accident, a fire or the like. This is a feature which has helped this apparatus to be approved by the Swedish National Institute of Radiation Protection.

In the plug 15 a capsule 18 is fitted, said capsule forming a conventional neutron radiation source containing, for instance, $^{239}$Pu-Be, $^{238}$Pu-Be, $^{241}$Am-Be, $^{244}$Cm-Be, $^{210}$Po-Be or $^{252}$Cf. Furthermore, a lead plug 19 is fitted in the plug 15 to form a shielding means for preventing gamma radiation from the neutron source in the direction covered by the lead plug 19. This is important since the neutron source emits a certain amount of gamma radiation which may be disturbing for the measurements. A small polythene plug 20 keeps the lead plug 19 and neutron source capsule 18 in position in the unit 15. The arrangement of the neutron source and capsule within the easily movable unit 15 permits the neutron source and unit 15 to be quickly moved and handled by non-qualified personnel, which is obviously of great advantage if a situation should occur which calls for rapid action. The unprotected neutron source capsule 18 may according to the regulations for protection against radiation only be handled by qualified personnel having special permits or authorization. As an alternative the neutron source could be moved automatically to a sheltered place by pneumatical or mechanical means. Such an arrangement is, however, very much more complicated than the present arrangement.

The invention is not limited to the use of one neutron source 18 but includes the arrangement of two or several sources in one or more units or plugs 15. The radiation may in this way be spread to form a band across a conveyor 9.

In the upper container 7 a vessel 21 is fitted which is filled with boron-containing polythene 22 and has a casing 23 embedded therein. At the inner end of said casing a scintillation detector 24 is fitted. Said detector may comprise a NaI (Tl) crystal with a photomultiplier and a pre-amplifier and outside thereof an amplifier 25. The photomultiplier is provided with electric power from a high voltage power supply unit 32. The amplifier 25 may preferably be combined with a spectrum stabilizer 26, FIG. 5, of well known design which serves to stabilize the measurement to a portion of the spectrum within which the registration takes place, for instance the 7.64 MeV line of the iron spectrum. As reference line for the stabilization in the described example of the invention the gamma radiation at 2.23 MeV may be utilized which occurs at the neutron capture in the hydrogenous materials in the plug 15 and the containers 5 and 7. The radiation captured by the detector 24 results in a signal, which over the amplifier 25 and the spectrum stabilizer 26 is conducted to a pulse height analyzer 27 and a rate meter 28 or scaler 29 and recorder 30, digital printer 31 or data logger 35 or timer 34, as illustrated diagrammatically in FIG. 5.

When the method according to the invention is applied to the handling of crushed ore, e.g. hematite, which is transported on a conveyor belt 9 of rubber the measuring apparatus is disposed with the container 5 below and the container 7 above the conveyor 9 which is achieved by pushing the carriage 3 from one side of the conveyor on the channels 2,2 at the measuring location 11.

Figure 5:
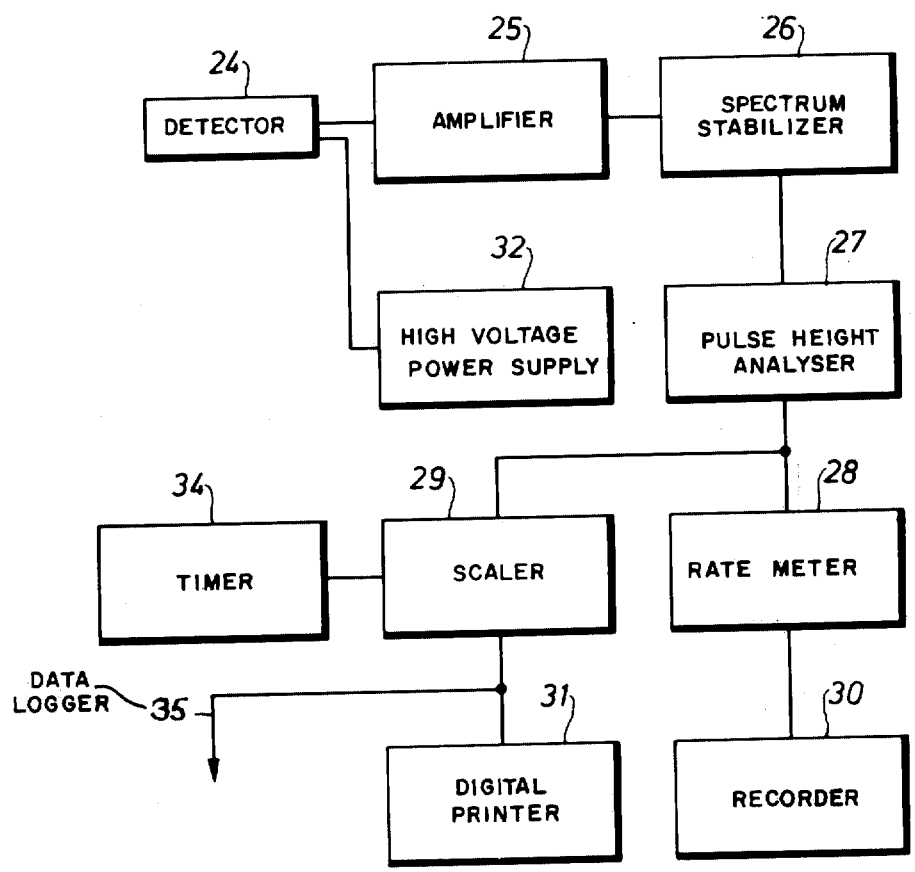
FIG. 5 shows diagrammatically a wiring diagram and the basic arrangement of the electrical equipment of the measuring apparatus.

The unit or plug 15 is picked up from its radiation shelter locker and is fitted in the container 5 with the aid of the handle 17 and is locked in position by the cross bolt 16. The electrical equipment according to FIG. 5 is connected. When the spectrum stabilizer has been locked to the reference gamma line, the measurement may start immediately. It should then be observed that the measurement may be carried out with the conveyor at rest or at full speed, since the measuring result has proved to be independent of the velocity of the material. Consequently, the measurement does not influence the operation of the conveyor. In order to check the function of the measuring apparatus an iron plate 33 is provided which, when no material is on the conveyor, is inserted between the conveyor and the container 5 and which produces a reference value for the radiation captured by the detector 24 when a certain amount of iron is present.

It is also possible to use two or more reference iron plates or the like corresponding to two or more concentrations of iron. During the practical measurement on the material 10 the iron plate 33 is naturally removed. When the conveyor moves, the scraper 12 regulates the proper material thickness at the measuring location 11.

As above indicated, the neutron source 18 apart from emitting neutron radiation also emits a certain amount of gamma radiation which might reach the detector and disturb the measurement. Said gamma radiation is effectively attenuated by the lead shield 19 which, however, has very little influence on the neutron radiation. The neutrons are emitted from the source 18 in all directions and collide several times with the hydrogen nuclei in the surrounding material in the plug 15 and the container 5. Said collisions reduce and equalize the velocity (=energy) of the originally fast neutrons to a level corresponding to the thermal energy of the surrounding material and so-called thermal neutrons are obtained. This process is called moderation and the hydrogen containing material in the plug 15 and the container 5 consequently serves as a moderator for the neutrons which get an energy distribution which considerably increases the probability of the desired capture of neutrons in the material 10 to be measured.

Some of the neutrons are also captured by the hydrogen-containing material and hereby provide the above mentioned reference gamma line at the energy 2.23 MeV. Furthermore, the hydrogen containing material also serves as radiation protection for the personnel which may be in the immediate vicinity of the apparatus. Consequently, the hydrogen-containing material has a threefold purpose, i.e. to function as moderator, as radiation shelter and as producer of the gamma energy reference line for the spectrum stabilizer 26.

A portion of the neutron radiation passes the material 10 without being captured thereby. In order to utilize as much as possible of the neutron radiation the container 7 with hydrogen-containing material is disposed on the upper side of the material 10, so that neutrons are scattered back to the material 10. The hydrogen-containing material in the upper container 7 functions in the same way as the hydrogen-containing material in the container 5 and plug 15, i.e. as moderator, as radiation shield, and as producer of a gamma energy reference line.

The hydrogen-containing material in the containers 5 and 7 is preferably water and has then a further function, i.e. as fire protection for the radiation source 18. The contents in said source are highly radio-toxic, so that spreading thereof by violence or accidents must be prevented.

The containers 5 and 7 should be completely filled, if the moderator 13, 14 is a liquid. The containers should then be connected to suitable expansion chambers.

The thermal neutrons from the moderators are captured by (and stay in) the nuclei of the material 10 and thereby immediately produce an emission of gamma rays, the energy of which (or wave length) is characteristic of the emitting nucleus (basic element). This is called prompt gamma ray emission. A certain neutron moderation may also take place in the material 10 itself. In connection with iron analyses we utilize the nuclear reaction:

$$^{56}Fe + n = ^{57}Fe + \gamma$$

in which n indicates the thermal neutrons and $\gamma$ the characteristic gamma radiation which is emitted promptly upon the capture of the neutrons. There are several different gamma lines. As above mentioned we have chosen to carry out the measurement within the high energy interval of the iron gamma spectrum on the dominating 7.64 MeV line. The iron isotope $^{56}Fe$ is stable (not radio-active) and has an abundance of 91.7% in natural iron. The produced $^{57}Fe$ isotope is also stable.

The characteristic gamma radiation from the material 10 is emitted in all directions and a portion of the radiation is absorbed in the detector crystal 24. The detector 24 is shielded against neutron radiation, which may have passed the moderators 5, 7 and the material 10 without being captured, by a boron-containing polyethene body 22 in a vessel 21. Neutron radiation may in certain processes give rise to disturbing signals from the detector and such influence may be suppressed by the boron-containing plastic 22 in the vessel 21. The suppression is obtained since the neutrons are moderated by the hydrogenous material and then captured by the boron which is a substance with great ability to absorb thermal neutrons.

The detector signal is fed through the amplifier 25 and the spectrum stabilizer 26 to the pulse height analyser. The spectrum stabilizer is set for selective measurement of the reference gamma radiation. Through feed-back to the pulse amplifier 25 or the high voltage power supply 32 it causes the reference line always to remain in a certain position in the radiation energy spectrum represented by the apparatus. The energy distribution is produced by electronic sorting of the detector pulses in the pulse height analyser 27. Said analyser is so arranged that it is easy to obtain a measurement of a desired portion of the gamma ray spectrum and to feed the result in analogous form through the rate meter 28 and recorder 30 or in digital form through the scaler 29 and the digital printer 31. Feeding of the result to a computer for process control equipment control may also be achieved by the data logger 35, as indicated in FIG. 5. The equipment consequently makes possible a continuous selective quantitative measurement of the gamma radiation within a certain energy interval which is stabilized against energy drift. Data collection during certain periods and with a desired periodicity is carried out in a simple way by means of a time recorder or program work, which may be controlled by the movement of the conveyor 9. The rate meter and recorder 30 may be used to provide momentary information regarding the iron concentration in the material 10 forwarded on the conveyor belt 9, whereas the scaler 29 and the digital printer give information of the integrated values, i.e. the total iron quantity in the material 10 forwarded during a certain time period.

In connection with iron measuring the apparatus is set for measuring gamma rays in a certain interval around the 7.64 MeV line, which is characteristic for iron. The pulse rate, i.e. the number of pulses measured during a time unit is then related to the iron content of the material 10. The relationship may, as mentioned above, be made practically linear within a concentration interval of limited extension, for instance 30 – 40%, 40 – 50% or 50 – 60% Fe and with a controlled height of material on the conveyor. Said height should not exceed a certain maximum value, since internal shielding of the gamma rays in the material 10 may otherwise occur. The maximum height of the material depends on the composition of the material. A larger concentration interval may naturally be covered if a non-linear calibrating curve is accepted.

The equipment according to the invention may be used for measuring dry material. However, if the material is wet, it is suitable to arrange a sprinkler before the measuring location so that a comparatively high moisture content is obtained. The influence of moisture content on the measuring result can then be kept constant and is easily controlled.

The relationship between pulse rate and iron concentration in a certain installation is established by conventional analyses and calibrations.

What we claim is:

1. In the method of measuring the concentration of a component in a material sample, which at the measuring location is at rest or moves as a stream of material, that improvement which includes
   irradiating said sample with thermally-moderated neutrons and detecting resultant gamma ray emission from said sample to provide a base line measurement;
   irradiating said sample with unmoderated neutrons to provide a gamma ray emission from said sample and measuring same; and
   determining said concentration by comparison of known gamma ray emissions relative to concentration
   whereby the concentration of said component in said material sample may be determined.

2. The method according to claim 1 including shielding the unmoderated neutron source to prevent gamma rays from said source reaching the measuring means.

3. The method according to claim 1 including substituting at least one reference plate containing known quantities of the component to be measured for said material sample and thereby calibrating said measuring means.

4. Apparatus for measuring the concentration of a component in a material sample comprising a radioactive neutron source and a gamma ray detector, said apparatus being characterized by the provision of a first neutron moderator surrounding said neutron source, shielding means for protecting the detector from direct gamma radiation from the neutron source, a second neutron moderator surrounding the detector, shielding means for protecting the detector for neutrons emitted from the neutron source, and means for transforming the gamma rays captured by the detector to a signal and for transmitting the signal to a recording device.

5. Apparatus according to claim 4, in which the neutron source is disposed in hydrogenous material, which together with the neutron source is formed as a unit adapted to be inserted and fixed in a first neutron moderator in a first container, and in which the detector is surrounded by a second neutron moderator and is disposed in a second container, said containers being carried by a frame at a distance from one another so that a measuring location for the material is formed between the containers, means for shielding the detector from gamma rays radiated directed from the neutron source, means for shielding the detector from neutron radiation from the neutron source, means for supplying electric power to the detector, and means for transforming the gamma rays captured by the detector to a signal and for transmitting said signal to the recording device.

6. Apparatus according to claim 5, in which the unit consists substantially of hydrogenous material of the group including paraffin and polythene in which the neutron source is fixed in the first moderator in a location so selected that the unit together with the neutron source may be rapidly moved to or from said location with consequent minimized risk of exposure to the personnel.

7. Apparatus according to claim 5, in which shielding means of lead are provided in the unit on the side of the neutron source facing the detector, so that the detector is protected against direct gamma radiation from the neutron source.

8. Apparatus according to claim 6, in which the first neutron moderator consists of water in a container in which the unit is fixed in the selected location.

9. Apparatus according to claim 5, in which the second neutron moderator consists of water in a container in which the detector is fixed in a location, in which it is protected against direct gamma and neutron radiation from the neutron source.

10. Apparatus according to claim 9, in which the detector is surrounded by shielding means comprising hydrocarbon polymer material containing boron.

11. Apparatus according to claim 5, in which the second neutron moderator consists of polythene.

12. Apparatus according to claim 5, in which the frame and the containers define a gap open on three sides, so that the frame and the containers from one side of a conveyor belt may be brought into a position with the first container below and the second container above the conveyor belt, on which the material is transported.

13. Apparatus according to claim 12, in which at least one reference plate is inserted between the first and the second container and the conveyor.

14. Apparatus according to claim 5, in which a spectrum stabilizer is connected in series with the detector and utilizes the gamma radiation with energe 2.23 MeV which during the neutron capture is emitted by the hydrogen of the moderators for stabilizing the measuring system and counteracting drift of the electronic equipment.

15. Apparatus according to claim 4 in which the neutron source is $^{241}$Am-Be.

16. Apparatus according to claim 4 in which the neutron source is $^{252}$Cf.

* * * * *